US012478761B1

(12) United States Patent
Ayoub

(10) Patent No.: US 12,478,761 B1
(45) Date of Patent: Nov. 25, 2025

(54) DECORATIVE PATCHES AND METHODS OF USING DECORATIVE PATCHES

(71) Applicant: Christine Ayoub, Newport Beach, CA (US)

(72) Inventor: Christine Ayoub, Newport Beach, CA (US)

( * ) Notice: Subject to any disclaimer, the term of this patent is extended or adjusted under 35 U.S.C. 154(b) by 0 days.

(21) Appl. No.: 18/803,498

(22) Filed: Aug. 13, 2024

(51) Int. Cl.
*A61F 5/00* (2006.01)
*A61F 13/00* (2024.01)
(Continued)

(52) U.S. Cl.
CPC ....... *A61M 21/02* (2013.01); *A61F 13/00059* (2013.01); *A61F 13/041* (2013.01);
(Continued)

(58) Field of Classification Search
CPC ........ A61F 13/04; A61F 13/041; A61F 13/58; A61F 5/0585; A61F 13/02; A61F 2013/00817; A61F 15/02; A61F 2210/0085; A61F 5/0127; A61F 5/0195; A61F 5/05; A61F 13/023; A61F 13/0206; A61F 13/0209; A61F 13/5622; A61F 15/004; A61F 13/0246; A61F 13/0253; A61F 13/0276; A61F 13/141; A61F 2013/0296; A61F 13/0203; A61F 13/0226; A61F 13/0259; A61F 13/15; A61F 13/42; A61F 13/00063; A61F 2013/00608; A61F 2013/00855; A61F 5/08; A61F 13/00085; A61F 13/0256; A61F 13/0269; A61F 13/0273; A61F 13/10; A61F 2/80; A61F 2210/0076; A61F 2240/001;
(Continued)

(56) References Cited

U.S. PATENT DOCUMENTS 2,862,846 A * 12/1958 Blackford ........... A61F 13/0279 602/42
3,255,748 A 6/1966 Wallerstein
(Continued)

FOREIGN PATENT DOCUMENTS

CN 2407741 Y * 11/2000
GB 2375305 A * 11/2002 ............. A61F 13/04

OTHER PUBLICATIONS

Dixley, Pricilla et al., Do cartoon stickers given after a hemoglobin finger stick influence preschoolers' pain perception, Journal Pediatric Health Care,Nov.-Dec. 2008;22(6):378-82 (Year: 2008).*
(Continued)

*Primary Examiner* — Kim M Lewis
(74) *Attorney, Agent, or Firm* — Procopio, Cory, Hargreaves & Savitch LLP

(57) ABSTRACT

Decorative patches and methods of using decorative patches are described herein. Contemplated methods can provide non-pharmacological analgesia to a patient having a cast after a medical procedure. Contemplated decorative patches can comprise a first material layer and a second adhesive layer. In some aspects, the first material layer can comprise a napped fabric material. In some aspects, the second adhesive layer can comprise a zinc-oxide containing adhesive. In some aspects, the first material layer and the second adhesive layer can compose a moleskin adhesive such as those used for blisters.

18 Claims, 2 Drawing Sheets

(51) Int. Cl.
*A61F 13/04* (2006.01)
*A61M 21/02* (2006.01)
*C09J 7/29* (2018.01)
*C09J 7/38* (2018.01)
*C09J 11/04* (2006.01)
*G09F 3/02* (2006.01)
*G09F 3/10* (2006.01)
*A61M 21/00* (2006.01)

(52) U.S. Cl.
CPC ................. *C09J 7/29* (2018.01); *C09J 7/383* (2018.01); *C09J 11/04* (2013.01); *G09F 3/02* (2013.01); *G09F 3/10* (2013.01); *A61M 2021/005* (2013.01); *A61M 2205/59* (2013.01); *G09F 2003/0225* (2013.01); *G09F 2003/0241* (2013.01); *G09F 2003/0266* (2013.01)

(58) Field of Classification Search
CPC ...... A61F 13/00987; A61F 13/53; A61F 2/08; A61F 2/76; A61F 2013/00646; A61F 2013/00795; A61F 2013/00906; A61F 5/0193; A61F 5/05841; A61F 7/007; A61F 7/034; A61F 13/00; A61F 13/0213; A61F 13/048; A61F 13/12; A61F 13/145; A61F 13/146; A61F 13/496; A61F 13/514; A61F 13/56; A61F 13/5633; A61F 15/008; A61F 2/5046; A61F 2002/5053; A61F 2013/00102; A61F 2013/00268; A61F 2013/00655; A61F 2013/00825; A61F 2013/15016; A61F 2013/422; A61F 5/0118; A61F 13/00051; A61F 13/00055; A61F 13/01012; A61F 13/01021; A61F 13/01029; A61F 13/025; A61F 13/0283; A61F 13/046; A61F 13/05; A61F 13/06; A61F 13/107; A61F 13/124; A61F 13/15577; A61F 13/471; A61F 13/472; A61F 13/475; A61F 13/4915; A61F 13/494; A61F 13/495; A61F 13/511; A61F 13/5512; A61F 13/5655; A61F 15/00; A61F 2/60; A61F 2/82; A61F 2002/043; A61F 2002/30583; A61F 2002/502; A61F 2002/5047; A61F 2002/5081; A61F 2002/7695; A61F 2013/0017; A61F 2013/00174; A61F 2013/00251; A61F 2013/00412; A61F 2013/00536; A61F 2013/00553; A61F 2013/00663; A61F 2013/00702; A61F 2013/00744; A61F 2013/00889; A61F 2013/15048; A61F 2013/4958; A61F 2013/53445; A61F 2013/53966; A61F 2013/5666; A61F 5/00; A61F 5/01; A61F 5/058; A61F 5/05866; A61F 5/44; A61F 11/14; A61F 13/00076; A61F 13/022; A61F 13/0289; A61F 13/045; A61F 13/064; A61F 13/067; A61F 13/069; A61F 13/15609; A61F 13/15658; A61F 13/36; A61F 13/4752; A61F 13/4753; A61F 13/49; A61F 13/49011; A61F 13/49017; A61F 13/4902; A61F 13/493; A61F 13/49413; A61F 13/51; A61F 13/51496; A61F 13/551; A61F 13/5514; A61F 13/60; A61F 13/84; A61F 2/20; A61F 2/2846; A61F 2/30965; A61F 2/4405; A61F 2/442; A61F 2002/206; A61F 2002/30064; A61F 2002/30072; A61F 2002/30909; A61F 2002/3092; A61F 2013/00093; A61F 2013/00119; A61F 2013/00229; A61F 2013/00238; A61F 2013/00263; A61F 2013/00272; A61F 2013/004; A61F 2013/00489; A61F 2013/00544; A61F 2013/0057
USPC .......................................................... D24/189
See application file for complete search history.

(56) References Cited

U.S. PATENT DOCUMENTS

| | | | | |
|---|---|---|---|---|
| 4,782,106 | A | 11/1988 | Fricke et al. | |
| 5,110,655 | A * | 5/1992 | Engler | G08B 5/004 2/5 |
| D783,844 | S | 4/2017 | Cyburt | |
| 2009/0053451 | A1 * | 2/2009 | Smith | B44C 1/1712 156/289 |
| 2011/0011517 | A1 | 1/2011 | Wood | |
| 2012/0145303 | A1 * | 6/2012 | McClarnan | B44C 1/10 156/60 |
| 2016/0193086 | A1 | 7/2016 | Castle | |

OTHER PUBLICATIONS

Wayback Machine—Apr. 11, 2021 (Apr. 2021)—Seton—Jaybird & Mais Moleskin Bandage Rolls 55/1250T. (Year: 2021).
https://www.performancehealth.com/rolyan-moleskin-strips-rolls.
https://www1.seton.com/jaybird-mais-moleskin-bandage-rolls-ca2014-5409c.html.
https://www.medline.com/jump/product/x/Z05-PF42262.
https://instagram.com/dr.artsandcasts?utm_medium=copy_link.
https://inside.choc.org/choc-anesthesiologist-brightens-patients-surgeries-bringing-a-cast-of-characters/ ; Published on: Jan. 19, 2022, 3 pages.

* cited by examiner

DECORATIVE PATCHES AND METHODS OF USING DECORATIVE PATCHES

TECHNICAL FIELD

This disclosure relates to decorative patches and related methods.

SUMMARY

In some aspects, a method of providing non-pharmacological analgesia (pain relief or reduction in pain) to a patient having a cast after a medical procedure is provided, comprising applying a decorative patch to a surface portion of the cast, wherein the decorative patch is capable of remaining adhered to the surface portion of the cast without peeling through a pain management period after the cast is put on the patient. For example, the decorative patch can be capable of remaining adhered to the surface portion of the cast without peeling through an entire pain management period after the cast is put on the patient. In some aspects, the decorative patch can be capable of remaining adhered to the surface portion of the cast without significant peeling (e.g., with at least 98% of the entire adhesive layer of the decorative patch remaining adhered to the surface portion of the cast) through an entire pain management period after the cast is put on the patient.

The pain management period may be any suitable length of time, for example, at least 12 hours after the cast is placed on the patient, 12 hours after the cast is placed on the patient, at least 24 hours after the cast is placed on the patient, 24 hours after the cast is placed on the patient, at least 36 hours after the cast is placed on the patient, 36 hours after the cast is placed on the patient, at least 48 hours after the cast is placed on the patient, 48 hours after the cast is placed on the patient, at least 72 hours after the cast is placed on the patient, 72 hours after the cast is placed on the patient, at least 1 week after the cast is placed on the patient, at least 2 weeks after the cast is placed on the patient, up to 12 hours after the cast is placed on the patient, up to 24 hours after the cast is placed on the patient, up to 36 hours after the cast is placed on the patient, up to 48 hours after the cast is placed on the patient, up to 72 hours after the cast is placed on the patient, up to 1 week after the cast is placed on the patient, up to 2 weeks after the cast is placed on the patient, or any other suitable time period.

In some embodiments, applying the decorative patch results in a lower pain score during the pain management period, and wherein the pain score is at least one of a visual analog scale (VAS) score and a face, legs, activity, cry, consolability (FLACC) score. In some aspects, applying the decorative patch results in a lower pain score during the pain management period, wherein the pain score is measured at a set time during the pain management period (e.g., during a time period 40-60% through the pain management period). In some aspects, applying the decorative patch results in a lower pain score during the pain management period compared to one or more other patients who have had the same medical procedure but do not have the decorative patch applied to their cast(s). In some aspects, applying the decorative patch results in a lower pain score during the pain management period compared to one or more other patients who have had the same medical procedure as the decorated cast patient (e.g., within a few years of, within a year of, within 6 months of, within a month of, within two weeks of, within a week of, or even within 24 hours of the decorated cast patient), but that do not have the decorative patch applied to their cast(s), wherein such other patient(s) not having the decorative patch applied to their cast(s) have one or more of the following (relative to the patient having the decorated cast patient): same age±10%, same age±20%, same sex, same laterality, same BMI±10%, same BMI±20%, same fracture type, same surgical time±10%, same surgical time±20%, same surgical time±30%, same anesthesia time±10%, same anesthesia time±20%, same anesthesia time±30%, same pain medication±10% (dose and frequency), same pain medication±20% (dose and frequency).

In some embodiments, the decorative patch comprises a first material layer and a second adhesive layer, and wherein applying the decorative patch comprises removing a backing from the decorative patch, and applying the second adhesive layer to the surface portion of the cast. In some embodiments, the decorative patch is configured to be removed from the surface portion without leaving a residue of the second adhesive layer on the surface portion. In some embodiments, the first material layer comprises a fabric material, wherein the fabric material comprises a napped cotton, and wherein the second adhesive layer comprises a zinc-oxide. In some embodiments, the first material layer of the decorative patch has a first side and a second side, and wherein the first side comprises a design drawn or printed thereon, and wherein the second adhesive layer is applied to the second side of the first material layer, and wherein the second adhesive layer comprises a zinc-oxide.

In some embodiments, the first material layer of the decorative patch comprises a first side and a second side, and wherein the second adhesive layer of the decorative patch is applied to at least 98% of the second side of the first material layer. In some embodiments, the first material layer of the decorative patch comprises a first side and a second side, and wherein the second adhesive layer of the decorative patch is applied to only a portion of the second side of the first material layer. In some embodiments, the first material layer of the decorative patch comprises a first side and a second side, and wherein the second adhesive layer of the decorative patch is applied to an entire outer edge of the second side of the first material layer. In some embodiments, the decorative patch is configured to be removed from the surface portion leaving no more than 2% of the second adhesive layer on the surface portion. In some embodiments, the second adhesive layer of the decorative patch comprises a zinc-oxide and a rubber.

In some embodiments, the method of providing non-pharmacological analgesia further comprises removing the decorative patch from the surface portion of the cast; and applying an adhesive layer of a second decorative patch to the surface portion of the cast. In some embodiments, the surface portion comprises at least one of a fiberglass, a plaster, and a self-adherent wrap material.

In some embodiments, the method of providing non-pharmacological analgesia further comprises drawing or printing a design on a first side of the first material layer with an ink. In some embodiments, the decorative patch has a thickness of between 20-50 mils.

In some aspects, a decorative patch for removably adhering to a cast or other device is provided, comprising a first material layer having a first side and a second side, and a second adhesive layer applied to the second side of the first material layer. The first side can comprise a design drawn or printed thereon, or a design formed of one or more decorative materials and adhered or otherwise coupled thereto.

The first material layer can comprise any suitable material or materials, including for example, a cotton, a cotton sateen cloth fabric, a napped cotton (on one or both sides), a pile material (with piles on one or both sides), a napped fabric, a woven material, a leather, a felt, a linen, a cotton, a nylon, a flannel, and a latex. It should be appreciated that in some aspects the "first material layer" can comprise a single layer of a single material, a single layer of a combination of materials, or multiple layers of the same or different materials forming a single piece that alone would not adhere to a cast, and to which an adhesive layer can be applied.

The second adhesive layer can be made of any suitable adhesive materials, which can include, for example, a zinc-oxide, a silicone, a latex, an acrylic, an epoxy, a polyurethane, a polyimide, an acrylate, a rubber (e.g., an epoxidized natural rubber, acrylonitrile-butadiene rubber, or blend thereof), a silicone, a zinc-oxide and rubber, a combination thereof, or any other suitable adhesive materials. In some aspects, the second adhesive layer can comprise a zinc-oxide and rubber mixture. In some aspects, the second adhesive layer can comprise a zinc-oxide and rubber laminate. In some aspects, the second adhesive layer can comprise a zinc-oxide filled rubber. In some aspects, the second adhesive layer can comprise a rubber coated with zinc-oxide.

In some aspects, the second adhesive layer can comprise an adhesive film layer affixed to at least 90%, at least 98%, or 100% of an outer edge or perimeter of the second side of the first material layer. In some aspects, the second adhesive layer can comprise an adhesive film layer affixed to at least 80%, at least 90%, at least 98% or 100% of the second side of the first material layer. In some aspects, the adhesive film layer can comprise a hot melt adhesive, a reactive hot melt adhesive, a thermosetting adhesive, a pressure sensitive adhesive, a contact adhesive, or any other type of adhesives.

In some aspects, the first material layer and the second adhesive layer can compose a moleskin adhesive, for example, a moleskin adhesive roll typically for medical use that is cut to form the first material layer and the second adhesive layer of the decorative patch. Exemplary moleskin adhesives are described in U.S. Pat. No. 3,255,748, which is incorporated by reference in its entirety.

A release liner or backing paper may be provided over the second adhesive layer to prevent the adhesive surface from prematurely adhering to an object. The release liner can carry the decorative patch until it is ready to be peeled from the release liner and self-adhered to a cast or other device to be decorated.

The decorative patches contemplated herein can have any suitable thickness. In some aspects, the decorative patches have a thickness of between 20-50 mils, or between 30-40 mils. In some aspects the decorative patches have a greater thickness (e.g., 20 mils to 1.5 cm, 20 mils to 1 cm, 1-10 mm, 1-5 mm), for example when a thicker first material layer is used, when multiple material layers are included, or where the decorative design is formed of one or more decorative materials adhered to the first material layer.

A cast comprises an interior surface portion that faces and generally contacts the cast wearer's skin, and an exterior surface portion that is visible to the wearer as well as others while the cast is worn by the wearer. The decorative patches can be configured to be removed from an exterior surface portion of the cast or other device leaving no more than 10%, no more than 5%, or no more than 2% of the second adhesive layer on the exterior surface portion. Viewed from another perspective, when the decorative patches are removed after being adhered (e.g., self-adhered, not self-adhered) to an exterior surface portion for at least 24 hours, at least 48 hours, at least one week, or even two weeks or longer, at least 90%, at least 95%, or at least 98% of the second adhesive layer can be removed with the patch, leaving little to no residue on the exterior surface portion. The decorative patches can be configured to be removed from an exterior surface portion of a cast or other device without leaving a residue of an adhesive layer thereon. In some aspects, the exterior surface portion comprises at least one of a fiberglass, a plaster, and a self-adherent wrap material (also known as Coban). In some aspects, the decorative patch can remain self-adhered to the exterior surface portion of the cast or other object without peeling for at least 2 weeks, at least 1 week, at least 5 days, at least 3 days, at least 48 hours, or at least 24 hours. Viewed from another perspective, in some aspects the decorative patch can remain self-adhered to the surface portion via the second adhesive layer of the decorative patch alone and without any additional mechanical securing means, such as fasteners, tapes, strings, staples, or glue. Viewed from another perspective, in some aspects the decorative patch can remain self-adhered to the surface portion without any additional mechanical securing means separate from the decorative patch, such as fasteners, tapes, strings, staples, or glue.

In some aspects, a method of applying a decorative patch to a cast or other object is provided, comprising removing a backing from a decorative patch comprising a first material layer and a second adhesive layer; and applying the second adhesive layer to an exterior surface portion of the cast or other object, wherein the decorative patch is capable of remaining self-adhered to the exterior surface portion of the cast or other object without peeling for at least 2 weeks, at least 1 week, at least 5 days, at least 3 days, at least 48 hours, or at least 24 hours. It should be appreciated that in some embodiments, while a user may choose to apply additional pressure or force (directly or via another object) to detach the decorative patch from the surface portion of the cast or other device at any moment of use, such decorative patch is considered "capable" of remaining adhered without peeling if it would remain adhered without peeling absent such additional pressure or force.

It is contemplated that once the decorative patch is self-adhered, a user may choose to add additional security mechanisms such as fasteners for additional security or other purposes.

The first material layer can comprise any suitable material or materials, including for example, a fabric, a cotton, a cotton sateen cloth fabric, a napped cotton, a pile material, a napped fabric, a woven material, a leather, a felt, a linen, a cotton, a nylon, a flannel, and a latex.

The second adhesive layer can be made of any suitable adhesive materials, which can include, for example, a zinc-oxide, a silicone, a latex, an acrylic, an epoxy, a polyurethane, a polyimide, an acrylate, a rubber (e.g., an epoxidized natural rubber, acrylonitrile-butadiene rubber, or blend thereof), a silicone, a zinc-oxide and rubber, a combination thereof, or any other suitable adhesive materials. In some aspects, the second adhesive layer can comprise a zinc-oxide and rubber mixture. In some aspects, the second adhesive layer can comprise a zinc-oxide and rubber laminate. In some aspects, the second adhesive layer can comprise a zinc-oxide filled rubber. In some aspects, the second adhesive layer can comprise a rubber coated with zinc-oxide. In some aspects, the second adhesive layer can comprise an adhesive film layer affixed to at least 90%, at least 98%, or 100% of an outer edge or perimeter of the second side of the first material layer. In some aspects, the second adhesive layer can comprise an adhesive film layer affixed to at least 80%, at least 90%, at least 98% or 100% of the second side of the first material layer. In some aspects, the adhesive film layer can comprise a hot melt adhesive, a reactive hot melt adhesive, a thermosetting adhesive, a pressure sensitive adhesive, a contact adhesive, or any other type of adhesives.

In some aspects, the first material layer and the second adhesive layer compose a moleskin adhesive, for example, a moleskin adhesive roll that is cut to form the first material layer and the second adhesive layer of the decorative patch.

In some aspects, the decorative patches are adhered to a release liner or backing paper, and contemplated methods can comprise removing the decorative patches from the release liner prior to adhering the patches on a cast or other device.

The methods described herein can further comprise removing the decorative patch from the exterior surface portion of the cast or other object, and applying a second adhesive layer of a second decorative patch to the exterior surface portion of the cast. The second decorative patch can comprise a second material layer, and wherein the first material layer and the second material layer have different designs drawn, printed or adhered to thereon. Additionally or alternatively, the methods described herein can further comprise drawing, printing or adhering a design on the first side of the first material layer. Additionally or alternatively, the methods described herein can further comprise applying a sealing component over the design, for example, a fixative or preserving agent to prevent smudging, fading, or discoloration.

In some aspects, the decorative patches can be configured to be removed from an exterior surface portion of the cast or other device leaving no more than 10%, no more than 5%, or no more than 2% of the second adhesive layer on the exterior surface portion. Viewed from another perspective, when the decorative patches are removed after being adhered (e.g., self-adhered) to an exterior surface portion for at least 24 hours, at least 48 hours, at least one week, or even two weeks or longer, at least 90%, at least 95%, or at least 98% of the second adhesive layer can be removed with the patch, leaving little to no residue on the exterior surface portion. In some aspects, the decorative patches are configured to be removed from the exterior surface portion without leaving a residue of an adhesive layer thereon. In some aspects, the exterior surface portion comprises at least one of a fiberglass, a plaster, and a self-adherent wrap material.

In some aspects, a kit is provided comprising a set of decorative patches for removably adhering to a cast or other device, the set of decorative patches comprising a first patch and a second patch; wherein a first patch of the set of decorative patches comprises a first patch material layer having a first side and a second side, and a first patch adhesive layer applied to the second side of the first patch material layer; and wherein the second patch of the set of decorative patches comprises a second patch material layer having a first side and a second side, and a second patch adhesive layer applied to the second side of the second patch material layer.

In some embodiments, the first patch has a first design drawn, printed, or stamped thereon. In some embodiments, the second patch has a second design drawn, printed, or stamped thereon. In some embodiments, the first design and the second design are different. In some embodiments, the first design and the second design are the same. In some embodiments, the first patch and the second patch are adhered to a release liner prior to being removed from the release liner and adhered to the cast or other device. In some embodiments, the first patch material layer comprises a cotton. In some embodiments, the first patch adhesive layer comprises a zinc oxide containing adhesive.

Other advantages and benefits of the disclosed devices, components and methods will be apparent to one of ordinary skill with a review of the following drawings and detailed description.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

After reading this description it will become apparent to one skilled in the art how to implement the disclosed packaging, devices, components and methods in various alternative embodiments and alternative applications. However, all the various embodiments of the present disclosure will not be described herein. It is understood that the embodiments presented here are presented by way of an example only, and not limitation. As such, this detailed description of various alternative embodiments should not be construed to limit the scope or breadth of the present disclosure as set forth below.

Going to a hospital can be a daunting experience, especially for children with broken bones or in need of an operation. Parents, friends, physicians, nurses and other healthcare professionals strive to take the focus off of the medical procedure and onto things that bring the patients comfort, such as dolls, pets, flowers, desserts, or the patient's favorite movie or cartoon characters. Having a cast on for days, weeks or months can be stressful and limiting, and efforts have been made to make the experience more fun for patients. For example, doctors will apply casts with a favorite color material as the outer layer or exterior surface portion, or even a glow-in-the-dark cast material. As another example, the patient can have an exterior surface portion of their cast signed or drawn on with sharpies or other thick-tipped markers by friends and others. As yet another example, there are cast tattoos that can be placed on an exterior surface portion of a cast and heated with a hair dryer while pressing down on the decal.

Applicant appreciated the need for a less permanent and more interchangeable or modifiable solution to allow patients to have the look of their casts kept new and exciting, thereby reducing the negative feelings associated with wearing a cast for several weeks or months.

Figure 1A:
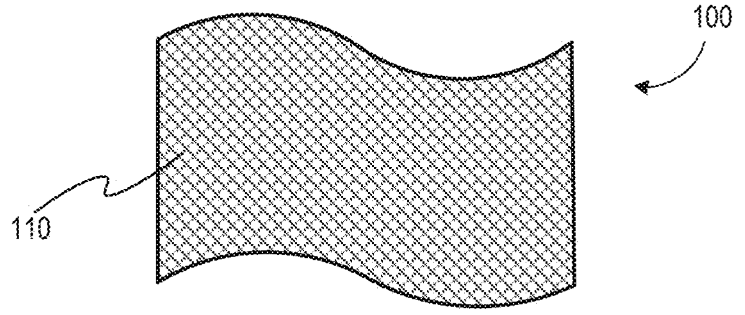
FIGS. 1A-1B illustrate the first material layer and second adhesive layer of a decorative patch, according to an embodiment.
Figure 1B:
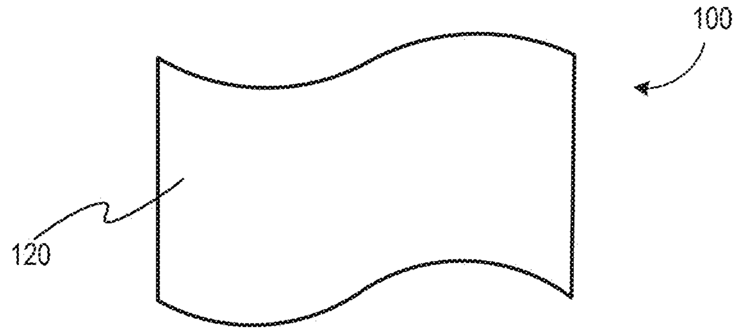

In the examples shown and described, decorative patches (with or without designs) for removably adhering to a cast or other device are provided. Now turning to FIGS. 1A-1B, a first material layer 110 and a second adhesive layer 120 of a patch 100 to be decorated is provided. The first material layer comprises a first side (shown in FIG. 1A) and a second side, and a second adhesive layer 120 applied to the second side of the first material layer 110. The first side can be drawn or printed on, or a design formed of one or more decorative materials or items can be adhered or otherwise affixed thereto.

The first material layer 110 can comprise any suitable material or materials, including for example, a cotton, a cotton sateen cloth fabric, a napped cotton, a flannel fabric with napped cotton backing, a combination of flannel, napped cotton, and rubber latex, a softly brushed napped cotton sateen fabric, a pile material, a napped fabric, a woven material, a leather, a felt, a linen, a cotton, a nylon, a flannel, a wool, a latex, or any combination thereof. Without wishing to be bound by any particular theory, a moleskin material such as a napped material or pile material may be especially suitable for the material layer. Such material can be easy to draw or print on (absorbs ink without bleeding), soft, easy to cut and trim, durable, difficult to wrinkle, thin without adding substantial bulk to the object it is applied to, and can provide a non-smooth surface for the adhesive layer to better adhere to. When the adhesive layer 120 is applied to the first material layer 110, the adhesive layer 120 can appear woven or non-smooth to an extent, which may assist in keeping the decorative patch self-adhered to the cast for at least 24 hours, at least 48 hours, at least 3 days, at least 5 days, at least one week, or even at least two weeks or longer where desired.

The second adhesive layer 120 (see also second adhesive layer 220 in FIG. 2) can be made of any suitable adhesive materials, which can include, for example, a zinc-oxide, a latex-free and hypo-allergenic zinc oxide adhesive, an epoxy, a polyurethane, a polyimide, an acrylate, a rubber, a silicone, a combination thereof, or any other suitable adhesive materials. Without wishing to be bound by any particular theory, a zinc-oxide adhesive may be especially suitable for the second adhesive layer. Decorative patches with a zinc-oxide adhesive have been found to stay self-adhered to cast materials (e.g., fiberglass, plaster, Coban) for several days and up to at least two weeks without any significant peeling or raising of the self-adhered portions of the decorative patch from the cast, while easily being removed from the cast materials without leaving any residue (or any residue visible to naked eyes) behind. In some aspects, the second adhesive layer can comprise a zinc-oxide and rubber mixture. In some aspects, the second adhesive layer can comprise a zinc-oxide and rubber laminate. In some aspects, the second adhesive layer can comprise a zinc-oxide filled rubber. In some aspects, the second adhesive layer can comprise a rubber coated with zinc-oxide.

In some aspects, the second adhesive layer can comprise an adhesive film layer affixed to at least 90%, at least 98%, or 100% of an outer edge or perimeter of the second side of the first material layer. In some aspects, the second adhesive layer can comprise an adhesive film layer affixed to at least 80%, at least 90%, at least 98% or 100% of the second side of the first material layer.

In some aspects, the first material layer and the second adhesive layer compose a moleskin adhesive, for example, a moleskin adhesive roll that is cut to form the first material layer and the second adhesive layer of the decorative patch.

The decorative patches contemplated herein can have any suitable thickness. In some aspects, the decorative patches have a thickness of between 20-50 mils, or between 30-40 mils. In some aspects the decorative patches have a greater thickness (e.g., 20 mils to 1.5 cm, 20 mils to 1 cm, 1-10 mm, 1-5 mm), for example when a thicker first material layer is used, or where the decorative design is formed of one or more decorative materials adhered to the first material layer.

The decorative patches can be configured to be removed from an exterior surface portion of a cast or other object without leaving a residue of an adhesive layer thereon. In some aspects, the decorative patches are not applied to skin. In some aspects, the exterior surface portion comprises at least one of a fiberglass, a plaster, and a self-adherent wrap material. In some aspects, the decorative patch can remain self-adhered to the exterior surface portion of the cast or other object without peeling for at least 2 weeks, at least 1 week, at least 5 days, at least 3 days, at least 48 hours, or at least 24 hours. In some aspects, at least 90%, at least 95%, or even at least 98% of the decorative patch's second adhesive layer can remain self-adhered to the exterior surface portion of the cast or other object for at least one week, at least ten days, or at least two weeks.

Figure 2:
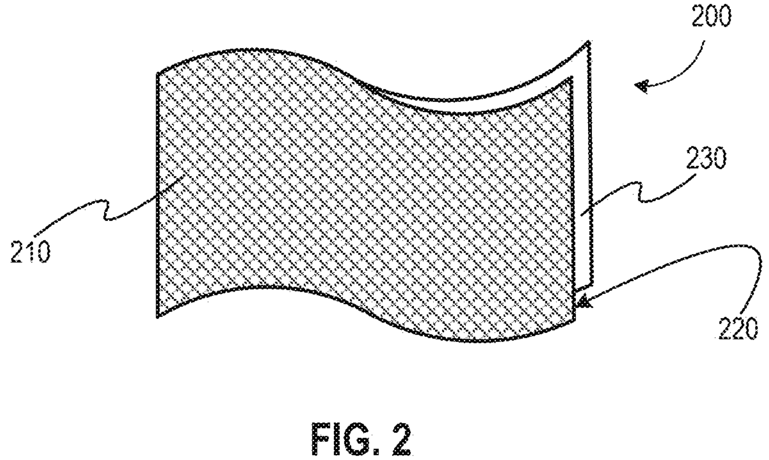
FIG. 2 illustrates another decorative patch being peeled off of a release liner, according to an embodiment.

As shown in FIG. 2, a release liner 230 or backing paper may be provided over the second adhesive layer 220 to prevent the adhesive surface from prematurely adhering. The release liner can carry the patch 200 with the first decorative material 210 exposed until it is ready to be peeled from the release liner and self-adhered to a cast or other device to be decorated.

In some contemplated embodiments, the first material layer can comprise several layers of material adhered to one another to form a single piece to which an adhesive can be applied. For example, the first material layer can comprise multiple layers of materials adhered to one another, with each of the material layers comprising any suitable material or materials, including for example, a foam, a padding, a cotton, a cotton sateen cloth fabric, a napped cotton, a flannel fabric with napped cotton backing, a combination of flannel, napped cotton, and rubber latex, a softly brushed napped cotton sateen fabric, a pile material, a napped fabric, a woven material, a leather, a felt, a linen, a cotton, a nylon, a flannel, a wool, a latex, or any combination thereof. In some aspects, the first and second sides of the first material layer can comprise a fabric to which an adhesive layer can be applied.

Materials Tested

Various materials and adhesives were tested on casts for suitability for decorative patches as contemplated herein, the results of which are summarized below.

Foam and glue. A foam material and glue adhesive were used to make a decorative patch. The foam and glue patch was too bulky for certain uses and came off completely in less than one day.

Fiberglass cast material. A fiberglass cast material with different colors than the cast to be decorated was cut and placed on the cast during the cast drying process. It was found that if placement of the patch on the cast was not timed correctly, the patch would come off immediately. Even when timed correctly, the edges of the patch were sharp, which could result in snagging onto clothing and bedding, as well as injury/scratching to the patient or others around the patient. Further, the patch would be permanently be incorporated into the cast when placed at the right time during the cast drying process.

Coban material. Designs were drawn on Coban material, which was then cut and placed onto a cast. The Coban patches were difficult to cut into clean shapes, and began curling up after only 1-2 days. Further, while the Coban material would initially stick to Coban material, it would not stick well to other materials of the cast (fiberglass, plaster).

Colored electrical tape. Colored electrical tape was not possible to draw on with the markers tested, and the tape left a residue when peeled from the cast.

Applicant also attempted to draw on the casts themselves, but only certain colors show up depending on the base cast/fiberglass color, and requires certain types of markers. Further, drawing on the cast would not allow a user to easily remove and replace the decorative designs.

Figure 3:
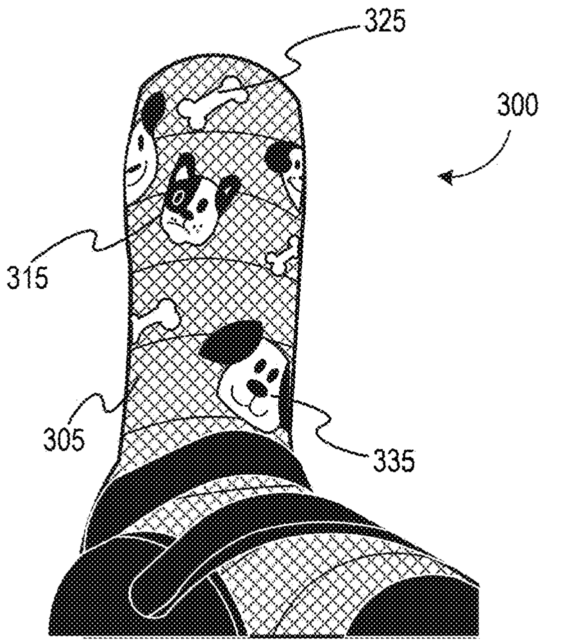
FIG. 3 illustrates a set of decorative patches self-adhered to a cast.
Figure 4:
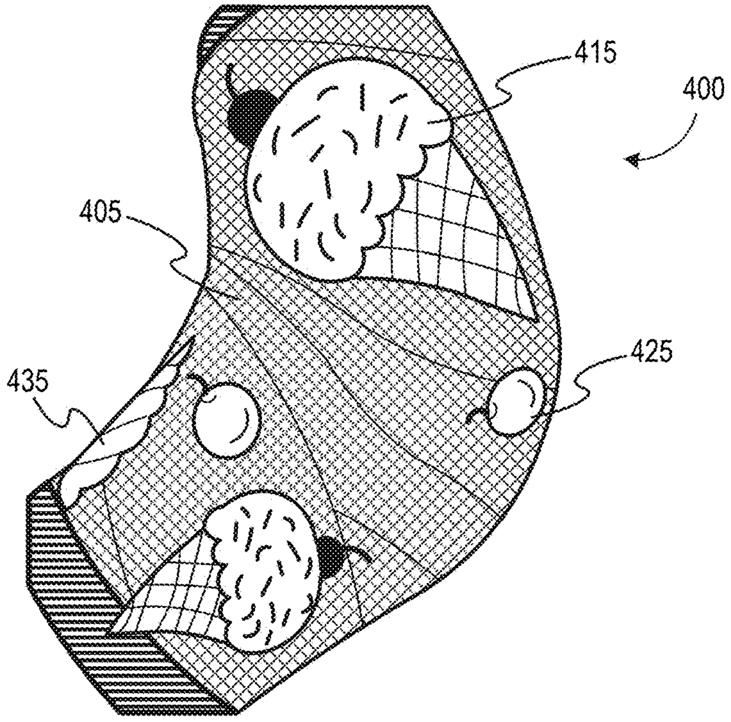
FIG. 4 illustrates another set of decorative patches self-adhered to a cast.

Moleskin. However, moleskin adhesive material (e.g., certain Jaybird and Mais moleskin rolls and Rolyan moleskin products) were found to stick well to cast material, including fiberglass, plaster and Coban material, for up to two weeks without significant peeling, while easily being removed without visible adhesive residue remaining on the cast. Further, the moleskin material was easy to draw on (absorbed ink without significant bleed), thin, and soft to the touch. FIG. 3 and FIG. 4 illustrate casts with exemplary decorative patches made using a moleskin adhesive material typically used to prevent blisters and irritation of skin.

As shown in FIG. 3, a decorated cast 300 comprising decorative patches 315, 325, 335 self-adhered to cast 305 is shown. Decorative patches 315, 325 and 335 comprise a first material layer (e.g., a material layer comprising at least one of napped cotton, flannel and rubber latex) and a second adhesive layer (e.g., a zinc-oxide containing adhesive; a zinc-oxide and rubber adhesive; a rubber adhesive). Similarly, FIG. 4 illustrates another decorated cast 400 comprising decorative patches 415, 425, 435 self-adhered to cast 405. Decorative patches 415, 425 and 435 comprise a first material layer (e.g., a material layer comprising at least one of a pile material and a napped material) and a second adhesive layer (e.g., a zinc-oxide containing adhesive; a zinc-oxide and rubber adhesive; a rubber adhesive). Casts 305 and 405 can each comprise any suitable cast material, including one or more of a fiberglass, a Coban or other self-adherent wrap material, and plaster.

It should be appreciated that contemplated decorative patches can comprise any suitable number of material and adhesive layers. It should also be appreciated that the decorative patches described herein can be used to decorate casts made of any suitable material as well as other devices such as splints, books, lockers, walls, vehicles, bicycles, skateboards, phone cases, mobile devices, windows, doors, clothing, and other devices made of any suitable materials (e.g., glass, plastic, metal, wood).

At least one layer (e.g., the outermost layer of the decorative patch) can include a design, which can be drawn, printed or otherwise included thereon. The designs can include any suitable design, including for example, a number, a letter, a symbol, a combination of numbers, a combination of letters, a combination of symbols, a combination of numbers, letters or symbols, an animal, a character, a sports team logo or name, sporting goods, a name, a slogan, a quote, a combination thereof, or any other suitable design. The design can be printed onto the decorative patch via a suitable printing method, or can be drawn thereon using any suitable inks and devices (e.g., crayons, pencils, markers, glitter pens, paint). Additionally or alternatively, one or more pieces of material separate from the first material layer and the second adhesive layer can be used to form a decorative design that is coupled to the at least one layer. For example, different pieces of material (e.g., leather, a felt, a cotton, a vinyl, a plastic) of different colors can be cut to form a decorative design that is then glued, sewn on, or otherwise coupled to a material layer, or one or more pieces of material separate from the first material layer and the second adhesive layer can be drawn on, printed on, or decorated with beads, sequins or other items to form a decorative design that is then glued, sewn on, or otherwise coupled to a material layer. Any combination of drawing, printing and coupling items to the at least one layer of the decorative patch can be utilized.

It is contemplated that the decorative patches described herein can be applied to certain objects, and when a change is desired, the decorative patches can be removed cleanly and replaced with a new decorative patch. In some aspects, a method of applying a decorative patch to a cast or other object is provided, comprising removing a backing or release paper from a decorative patch comprising a first fabric material layer and a second adhesive layer, and applying the second adhesive layer to an exterior surface portion of the cast or other object, wherein the decorative patch remains self-adhered to the exterior surface portion of the cast or other object without peeling for at least 2 weeks, at least 1 week, at least 5 days, at least 3 days, at least 48 hours, or at least 24 hours.

The first material layer can comprise any suitable material or materials, including for example, a cotton, a cotton sateen cloth fabric, a napped cotton, a pile material, a napped fabric, a woven material, a leather, a felt, a linen, a cotton, a nylon, a flannel, and a latex.

The second adhesive layer can be made of any suitable adhesive materials, which can include, for example, a zinc-oxide, a silicone, a latex, an acrylic, an epoxy, a polyurethane, a polyimide, an acrylate, a rubber (e.g., an epoxidized natural rubber, acrylonitrile-butadiene rubber, or blend thereof), a silicone, a zinc-oxide and rubber, a combination thereof, or any other suitable adhesive materials. In some aspects, the second adhesive layer can comprise a zinc-oxide and rubber mixture. In some aspects, the second adhesive layer can comprise a zinc-oxide and rubber laminate. In some aspects, the second adhesive layer can comprise a zinc-oxide filled rubber. In some aspects, the second adhesive layer can comprise a rubber coated with zinc-oxide.

In some aspects, the second adhesive layer can comprise an adhesive film layer affixed to at least 90%, at least 98%, or 100% of an outer edge or perimeter of the second side of the first material layer. In some aspects, the second adhesive layer can comprise an adhesive film layer affixed to at least 80%, at least 90%, at least 98% or 100% of the second side of the first material layer. In some aspects, the adhesive film layer can comprise a hot melt adhesive, a reactive hot melt adhesive, a thermosetting adhesive, a pressure sensitive adhesive, a contact adhesive, or any other type of adhesives.

In some aspects, the first material layer and the second adhesive layer compose a moleskin adhesive, for example, a moleskin adhesive roll that is cut to form the first material layer and the second adhesive layer of the decorative patch.

In some aspects, the decorative patches are adhered to a release liner or backing paper, and contemplated methods can comprise removing the decorative patches from the release liner prior to adhering the patches on a cast or other device. As described herein, it is contemplated that any suitable design can be included on the decorative patches (e.g., on the first fabric material layer), and that such designs can be drawn or printed thereon, a design element can be formed as a separate piece (or pieces) and glued, sewn or otherwise coupled to the decorative patches, or any combination thereof.

The methods described herein can further comprise removing the decorative patch from the exterior surface portion of the cast or other object, and applying a second adhesive layer of a second decorative patch to the same or different exterior surface portion of the cast. The second decorative patch can comprise a second material layer, and wherein the first material layer of the first patch and the second material layer of the second patch have different designs drawn, printed or adhered to thereon. Additionally or alternatively, the methods described herein can further comprise drawing, printing or adhering a design on the first side of the first material layer.

In some aspects, the decorative patches are configured to be removed from the exterior surface portion without leaving a residue of an adhesive layer thereon. In some aspects, the exterior surface portion comprises at least one of a fiberglass, a plaster, and a self-adherent wrap material.

Analgesic Study

Background; Introduction.

Attempting to comfort a child in a state of distress may require a multi-faceted approach. Whether it be through pharmacological agents and interventions or emotional and behavioral support, the ultimate goal is keep the patient and their family comfortable. One means of non-pharmacological support provided is personalized artwork applied to the bandages, casts, and splints of patient's returning from the operating room. No study to date has demonstrated the analgesic influence that cast art can provide. The care for the post-operative pediatric patient is multi-faceted with pharmacologic pain control as well as emotional and behavioral support. Distraction and redirection are highly documented means of combating situations of acute pain in adolescents. Child-life specialists have been deployed to aid in care of the perioperative adolescent by tailoring to the psychological, social, and intellectual needs of the patient. An interdisciplinary approach to pain control and de-escalating stressful situations not only provides comfort to the patient and the family present, but it also decreases pharmacologic burden to patients and the possible deleterious effects that come with it. This begs the question of in what other non-pharmacological ways can the perioperative pediatric patient be treated.

Through the advent and proliferation of social media the masses are more aware of these means of non-pharmacologic treatment. Celebrity appearances, dancing medical personnel and customized personal art have been seen as a way to alleviate the distress experienced by patients in situations of pain and fear. At a single Children's hospital it was found that an anesthesiologist, the inventor, was not only performing her physician duties but also acted as a child life specialist by creating personalized art that was placed onto postoperative bandages, casts, and splints. This led to the question of do patients who have received personalized art as a means of emotional and intellectual comfort display less pain and do they require less pharmacologic analgesic agents than a cohort who did not receive artwork.

The primary objective of this study was to determine if pediatric patients who underwent closed reduction with percutaneous pinning (CRPP) of a supracondylar humerus (SCH) fracture and subsequent casting with cast art applied in accordance with the cast art and methods described herein demonstrated lower pain scores than patients who did not receive cast art. A secondary measure of the study was to determine if the analgesic need, especially narcotic medications, were decreased in the cohort of patients who received cast art.

Methods.

Patient charts from a single institution who underwent closed reduction with percutaneous pinning of supracondylar humerus fractures who received anesthesia from the same singular anesthesiologist, the inventor, were queried from the Hospital's database. In the cast art group, cast art was applied during surgery. The charts were reviewed to record patient's Visual Analog Scale and FLACC scores and medication administration record (MAR) while they were in the post-operative anesthesia care unit (PACU) and on the medical-surgical floor (usually about 1 day). Chi-square, ANOVA and Man-Whitney U tests used to determine significance set as $P<0.05$.

An institutional board review was approved and retrospective chart review was performed to retrieve data from a single pediatric hospital. A list of 179 charts of patients who received intraoperative anesthesia for upper extremity injuries from a single anesthesiologist at Children's Hospital Orange County (Orange, California) were compiled from January-2018 through August-2023. Given the prevalence and operative treatment rate of supracondylar humerus fractures in the pediatric population, charts were queried for CPT 24538 (percutaneous skeletal fixation of supracondylar or transcondylar humeral fracture, with or without intercondylar extension). Seventy-six patient records matched the queried CPT code. Patients were excluded if they had concomitant injuries or underwent open reduction. Sixty-eight patient records were found to be appropriate for inclusion in the study. Pre-operative radiographs were analyzed by a senior level orthopedic surgery resident and fractures were classified based on the Gartland fracture classification. Demographic data such as age at time of injury, BMI, sex, laterality of injury, and Gartland fracture type were recorded for the selected charts. Additionally, surgical time and time under anesthesia were also recorded. Patients who fit inclusion criteria were divided into the control and cast art groups. The anesthesiologist who provided the cast art began applying the art in 2020, so surgeries occurring in 2018 and 2019 were included in the control group while surgeries occurring in 2021-2023 were included in the cast art group. To assess post-operative pain VAS (Visual Analog Scale) and FLACC (Face,Legs,Activity,Cry, Consolability) pain assessment tools were recorded from the patient's chart and separated between their time in the Post-operative anesthesia care unit (PACU) and on the medical-surgical floor post-operatively. An average from the range of all pain assessment recordings was calculated for the two groups again separated by location (PACU versus med-surg floor). Additionally, the medication administration record (MAR) was observed and all analgesic medications and doses were recorded and separated by whether the medication was administered in the PACU or on the med-surg floor.

Statistical analyses were conducted to compare demographic data among the control and cast art cohorts. The average of the patient's VAS and FLACC scores were compared between the two groups separating them from when they were obtained in the PACU and on the medical-surgical floor as were the class and dose of analgesic medications. Tests used included chi-square, ANOVA, and Man-Whitney U with alpha being set at $P<0.05$ for statistical significance.

Results.

As shown in Table 1 below, no statistically significant difference was found between the two groups regarding age of patient at time of injury, laterality of injury, BMI, sex, or fracture type based on the Gartland fracture classification. The control group had statistically significantly shorter surgery times (20.1+/−5.6 vs 24.6+/−8.4, p=0.012) and time under anesthesia (49.9+/−9.9 vs 59.9+/−19.4, p=0.01). No difference in VAS or FLACC scores were observed while the patients were in the PACU. The cast art group had significantly lower VAS (P=0.009) and FLACC (P=0.004) scores when the patients were observed on the floor. The cast art group had significantly lower number of patients who required tylenol on the floor (P=0.048), lower dose of ibuprofen given to patients on the floor (P=0.014), and most importantly four times less the amount of patients requiring narcotics on the floor (P=0.003).

Sixty-eight patients met inclusion criteria for this study and were separated into two cohorts. Thirty-five patients were placed in the control group and thirty-three in the cast art group. There was no difference in the age in months at time of injury between the control (69+/−26 m) and the cast art (71+/−28 m) groups. Patient sex was evenly divided (P=0.81) between the control (17 females 48.6%, 18 males 51.4%) and cast art (17 females 51.5%, 16 males 48.5%) group. No statistically significant difference in BMI (P=0.369) in the control (17.4+/−6.1 kg/m$^2$) versus the cast art (16.2+/−2.9 kg/m$^2$) groups. Gartland fracture classification was also found to be similarly divided between the two groups (P=0.995) with the control group having 11 (31.4%) Type II fractures, 23 (65.7%) Type III fractures, and 1 (2.9%) flexion type fractures. The cast art group had 10 (30.3%) Type II fractures, 22 (66.7%) Type III fractures, and 1 (3%) flexion type fractures.

When the surgical time and time under anesthesia were observed there was a statistically significant difference between the control group and the cast art group. There was a shorter duration of surgical time for the control group (20.1+/−5.6 vs 24.6+/−8.4, p=0.012) as well as a shorter time under anesthesia (49.9+/−9.9 vs 59.9+/−19.4, p=0.01).

Post-operative anesthesia care unit subjective pain scale ratings between the control and cast art groups did not distinguish a statistically significant difference. This was as expected with the patients in each group still under the influence of intraoperative analgesic medications and without the ability to recognize or realize the presence of artwork placed on their cast for their comfort. The PACU VAS average for the control group (0.57+/−1.16) had no significant difference (P=0.681) compared to the cast art group (0.55+/−0.89). The PACU FLACC score did demonstrate difference but not enough to yield statistical significance (P=0.433) with control group average (0.55+/−1.12) and the cast art average score of (0.29+/−0.7).

However, when the VAS and FLACC scores were again recorded on the med-surg floor, the cast art group on average demonstrated a statistically significant less amount of pain as they moved further away from the intraoperative analgesics. The average VAS score on the floor highly favored the cast art group (0.38+/−0.56 vs 1.12+/−1.25, P=0.009). A similar result was seen with the med-surg FLACC score (0.16+/−0.38 vs 0.73+/−0.87, P=0.004).

Post-operative required analgesia was also separated by where it was received (PACU vs floor) with class and dose of medication recorded to compare the two groups. In the PACU, there was no significant difference in analgesic administration (P=0.48). Analgesic medication was administered to seven (20%) control group patients with one patient receiving multimodal analgesia (received tylenol and narcotics) compared to nine (27.3%) in the cast art group where again one patient received multimodal analgesic agents (received tylenol and narcotics). Seven patients in the control and cast art group received narcotics in the PACU (20% vs 21%, P=0.9) with no significant difference in morphine milligram equivalents (MMEs) (0.87 vs 1.53, P=0.376).

When reviewing the medication administration record after the patients reached the medical-surgical floor is when the greatest difference in medication need was observed. The cast art cohort had 21 of its 33 patients receive some form of analgesic medication versus the control cohorts 24 of 35 patients (63.6% vs 68.6%, P=0.67). A statistically significant greater number of control patients received tylenol while on the floor compared to the cast art group (20, 57.1% vs 11, 33.3%, P=0.048). The average dose of the tylenol received between the two cohorts did not differ significantly (33.5 mg vs 458.36 mg, P=0.286). Number of patients who received ibuprofen on the floor was found to be similar, however the dose received did demonstrate that the control group required a statistically significant greater dose of ibuprofen than the cast art group (335.13 mg vs 213.36 mg, P=0.014). Toradol was administered in five patients in the cast art group (15.2%) compared to two (5.7%) in the control group (P=0.2) with almost no difference in the dosage (21.5 mg vs 20 mg, P=0.93). Most notable was the finding of the infrequent need for narcotics in the cast art group contrasted to the control group (3, 9.1% vs 14, 40%, P=0.003).

CONCLUSION

Patients undergoing CRPP for SCH fracture were found to have lower pain scores (VAS and FLACC) on the medical-surgical floor. Cast art patients also had decreased floor analgesic requirements. Accordingly, cast art disclosed herein in some embodiments provides clinical benefits in a form of nonpharmacological analgesia. With what is known about the need for a multidisciplinary approach to pediatric pain, cast art disclosed herein in some embodiments contributes to a form of holistic care provided to the patient. Without wishing to be bound by any particular theory, it is contemplated that the cast art and methods described herein advantageously allow patients and others to gain the full benefits of cast art as the cast art can remain adhered without peeling for at least 24 hours, at least 48 hours, or even longer, can be fully removable (without residue) and replaceable to allow cast art designs to be swapped, removed, added, moved, or modified.

DISCUSSION

A multidisciplinary approach to the treatment of pediatric patients experiencing pain has been demonstrated as a means to limit the need for significant amounts of pharmacological analgesic agents. By limiting the dependence on medications there is a direct ability to decrease deleterious effects that come with medications, specifically narcotics. Interacting with the patient and inquiring about hobbies, sports, and other interests can lead to distraction and relief of pain and anxiety, which is why child-life specialists are frequently deployed within children's hospitals. Taking the interaction with children and learning about their interests and going beyond that we have seen how cast art in the postoperative supracondylar humerus patient does actually demonstrate a decreased need for analgesic medications, specifically narcotics. Also revealed was the overall decrease in subjective pain score in children who received cast art.

The present disclosure specifically looked at this non-pharmacological intervention as a real means of analgesia and anxiolysis in the pediatric population, an insight heretofore unrecognized. Additionally, the present disclosure connected this facet of the multidisciplinary approach to pain as a real means of decreasing need for analgesic agents and resulting lower pain scores, an insight heretofore unrecognized.

In this study, one anesthesiologist was responsible for every patient's intraoperative anesthesia care resulting in a standardized form of pain control while undergoing surgery and while emerging. What led to the advent of this analysis was the fact that the same anesthesiologist was also the individual performing the multidisciplinary work of providing the cast art for the patients of the study. It also led to a natural blinding of the two retrospective groups as the pharmacological practice did not change but the integration of the non pharmacological resulted in what has been demonstrated as a less painful group of patients.

The cast art group of the study was found to have significantly lower VAS scores (P=0.009) and FLACC scores (P=0.004) while the patients were furthest away from the intraoperative analgesics they received. The cast art group had significantly less Tylenol use (P=0.048) and lower doses of ibuprofen (P=0.014) than their matched control cohort. Potentially the most important result was the finding that the cast art group had four times less patients requiring narcotic strength analgesics on the medical surgical floor postoperatively (P=0.03).

The patient stratification within this study stands out as a strength with nearly identical matching in regard to age, laterality of injury and most importantly severity of injury highlighted by the Gartland fracture classification. Having a single anesthesia provider limits variability in medication regimen intraoperatively which maintains consistency of treatment until the two were divided based on whether they received cast art or not.

Upon review there was not an observable consistent timeframe in which the VAS and FLACC scores had to be obtained in the PACU or on the floor resulting in a wide range of pain level recordings among the charts queried.

Patients within the cast art group were found to have statistically longer surgical times (P=0.012) and longer times under anesthesia (P=0.01). With each group having relatively the same amount of higher grade fractures, which would typically lend to increased operative times, that cannot be used as the explanation for increased time in the operating room. Although the intraoperative medication doses are not reported, no observable difference was seen during the data collection of the study. One possible explanation could be the influx of newly fellowship trained surgeons joining the practice that performed all of these surgeries during the same time frame that the cast art group was selected from.

TABLE 1

| | Control Group (n = 35) | Cast Art Group (n = 33) | P-value |
|---|---|---|---|
| Age (months) | 69 +/− 26 | 71 +/− 28 | |
| BMI (kg/m$^2$) | 17.4 +/− 6.1 | 16.2 +/− 2.9 | 0.369 |
| Sex | 17 Females (48.6%)<br>18 Males (51.4%) | 17 Females (51.5%)<br>16 Males (48.5%) | 0.81 |
| Laterality | Left 22 (62.9%)<br>Right 13 (37.1%) | Left 22 (66.7%)<br>Right 11 (33.3%) | 0.743 |
| Fracture Type (Gartland Fracture Classification) | Type II: 11 (31.4%)<br>Type III: 23 (65.7%)<br>Flexion Type: 1 (2.9%) | Type II: 10 (30.3%),,<br>Type III: 22 (66.7%)<br>Flexion Type: 1 (3%) | 0.995 |
| Surgical Time (min) | 20.1 +/− 5.6 | 24.6 +/− 8.6 | 0.012 |
| Anesthesia Time (min) | 49.9 +/− 9.9 | 59.9 +/− 19.4 | 0.01 |
| PACU VAS | 0.56 +/− 1.16 | 0.54 +/− 0.89 | 0.681 |
| PACU FLACC | 0.55 +/− 1.12 | 0.29 +/− 0.7 | 0.433 |
| PACU # of patients receiving medications | 7/35 (20%) | 9/33 (27.3%) | 0.48 |
| PACU # of patients receiving Tylenol | 7/35 (20%) | 9/33 (27.3%) | 0.52 |
| PACU average Tylenol dose | 280 mg | 208 mg | — |
| PACU # of patients receiving Toradol | 0/35 (0%) | 1/33 (3%) | 0.52 |
| PACU average Toradol dose | 0 mg | 15 mg | — |
| PACU # of patients receiving Narcotics | 7/35 (20%) | 7/33 (21%) | 0.9 |
| PACU average Narcotic MME | 0.87 MME | 1.53 MME | 0.376 |
| Floor VAS | 1.12 +/− 1.25 | 0.38 +/− 0.56 | 0.009 |
| Floor FLACC | 0.73 +/− 0.87 | 0.16 +/− 0.38 | 0.004 |
| Floor # of patients receiving medications | 24/35 (68.6%) | 21/33 (63.6%) | 0.67 |
| Floor # of patients receiving Tylenol | 20/35 (57.1%) | 11/33 (33.3%) | 0.048 |
| Floor average Tylenol dose | 333.5 mg | 213.36 mg | 0.286 |
| Floor # of patients receiving Ibuprofen | 8/35 (22.9%) | 11/33 (33.3%) | 0.34 |
| Floor average Ibuprofen dose | 335.13 mg | 213.36 mg | 0.014 |
| Floor # of patients receiving Toradol | 2/35 (5.7% | 5/33 (15.2%) | 0.2 |
| Floor average Toradol dose | 20 mg | 21.5 mg | 0.93 |
| Floor # of patients receiving Narcotics | 14/35 (40%) | 3/33 (9.1%) | 0.003 |
| Floor average Narcotic MME | 3.06 MME | 2 MME | 0.414 |

NON-LIMITING EMBODIMENTS

Embodiment 1. A decorative patch for removably adhering to a cast or other device, comprising: a first material layer having a first side and a second side, wherein the first side comprises a design drawn or printed thereon; and a second adhesive layer applied to the second side of the first material layer, wherein the second adhesive layer comprises a zinc-oxide.

Embodiment 2. The decorative patch of embodiment 1, wherein the first material layer comprises a cotton.

Embodiment 3. The decorative patch of any of embodiments 1-2, wherein the first material layer comprises a cotton sateen cloth fabric.

Embodiment 4. The decorative patch of any of embodiments 1-3, wherein the first material layer comprises a napped cotton.

Embodiment 5. The decorative patch of any of embodiments 1-4, wherein the first material layer comprises at least one of a leather, a felt, a linen, a cotton, a nylon, a flannel, and a latex.

Embodiment 6. The decorative patch of any of embodiments 1-5, wherein the decorative patch has a thickness of between 20-50 mils.

Embodiment 7. The decorative patch of any of embodiments 1-6, wherein the decorative patch has a thickness of between 30-40 mils.

Embodiment 8. The decorative patch of any of embodiments 1-7, wherein the second adhesive layer is applied to at least 98% of the second side of the first material layer.

Embodiment 9. A decorative patch for removably adhering to a cast or other device, comprising: a first fabric material layer having a first side and a second side, wherein the first side comprises a design drawn or printed thereon; and a second adhesive layer applied to the second side of the first material layer.

Embodiment 10. The decorative patch of embodiment 9, wherein the first fabric material layer comprises a cotton.

Embodiment 11. The decorative patch of any of embodiments 9-10, wherein the second adhesive layer comprises a zinc-oxide Embodiment 12. The decorative patch of any of embodiments 9-11, wherein the decorative patch has a thickness of between 20-50 mils.

Embodiment 13. The decorative patch of any of embodiments 9-12, wherein the second adhesive layer is applied to an entire outer edge of the second side of the first material layer.

Embodiment 14. A method of applying a decorative patch to a cast or other device, comprising: removing a backing from a decorative patch comprising a first fabric material layer and a second adhesive layer; and applying the second adhesive layer to a surface portion of the cast or other device, wherein the decorative patch is capable or remaining adhered to the surface portion of the cast or other device without peeling for at least 24 hours.

Embodiment 15. The method of embodiment 14, wherein the decorative patch is configured to be removed from the surface portion without leaving a residue of the second adhesive layer on the surface portion.

Embodiment 16. The method of any of embodiments 14-15, further comprising: removing the decorative patch from the surface portion of the cast or other device; and applying a second adhesive layer of a second decorative patch to the surface portion of the cast or other device.

Embodiment 17. The method of any of embodiments 14-16, wherein the second decorative patch comprises a second material layer, and wherein the first material layer and the second material layer have different designs drawn or printed thereon.

Embodiment 18. The method of any of embodiments 14-17, wherein the surface portion comprises at least one of a fiberglass, a plaster, and a self-adherent wrap material.

Embodiment 19. The method of any of embodiments 14-18, further comprising: drawing or printing a design on a first side of the first material layer with an ink.

Embodiment 20. The method of any of embodiments 14-19, wherein the first fabric material layer comprises a napped cotton, and wherein the second adhesive layer comprises a zinc-oxide.

Embodiment 21. A method of applying a decorative patch to a cast, comprising: removing a backing from a decorative patch comprising a first material layer and a second adhesive layer; and applying the second adhesive layer to a surface portion of the cast, wherein the decorative patch is capable of remaining adhered to the surface portion of the cast without peeling for at least 24 hours.

Embodiment 22. The method of embodiment 21, wherein the decorative patch is configured to be removed from the surface portion without leaving a residue of the second adhesive layer on the surface portion.

Embodiment 23. The method of any of embodiments 21-22, further comprising removing the decorative patch from the surface portion of the cast; and applying a second adhesive layer of a second decorative patch to the surface portion of the cast.

Embodiment 24. The method of any of embodiments 21-23, wherein the second decorative patch comprises a second material layer, and wherein the first material layer and the second material layer have different designs drawn or printed thereon.

Embodiment 25. The method of any of embodiments 21-24, wherein the surface portion comprises at least one of a fiberglass, a plaster, and a self-adherent wrap material.

Embodiment 26. The method of any of embodiments 21-25, further comprising drawing or printing a design on a first side of the first material layer with an ink.

Embodiment 27. The method of any of embodiments 21-26, wherein the first material layer comprises a fabric material, wherein the fabric material comprises a napped cotton, and wherein the second adhesive layer comprises a zinc-oxide.

Embodiment 28. The method of any of embodiments 21-27, wherein the first material layer of the decorative patch has a first side and a second side, and wherein the first side comprises a design drawn or printed thereon, and wherein the second adhesive layer is applied to the second side of the first material layer, and wherein the second adhesive layer comprises a zinc-oxide.

Embodiment 29. The method of any of embodiments 21-28, wherein the first material layer of the decorative patch comprises a cotton.

Embodiment 30. The method of any of embodiments 21-29, wherein the first material layer of the decorative patch comprises a cotton.

Embodiment 31. The method of any of embodiments 21-30, wherein the first material layer of the decorative patch comprises a cotton sateen cloth fabric.

Embodiment 32. The method of any of embodiments 21-31, wherein the first material layer of the decorative patch comprises at least one of a leather, a felt, a linen, a cotton, a nylon, a flannel, and a latex.

Embodiment 33. The method of any of embodiments 21-32, wherein the decorative patch has a thickness of between 20-50 mils.

Embodiment 34. The method of any of embodiments 21-33, wherein the decorative patch has a thickness of between 30-40 mils.

Embodiment 35. The method of any of embodiments 21-34, wherein the first material layer of the decorative patch comprises a first side and a second side, and wherein the second adhesive layer of the decorative patch is applied to at least 98% of the second side of the first material layer.

Embodiment 36. The method of any of embodiments 21-35, wherein the first material layer of the decorative patch comprises a first side and a second side, and wherein the second adhesive layer of the decorative patch is applied to an entire outer edge of the second side of the first material layer.

Embodiment 37. The method of any of embodiments 21-36, wherein the decorative patch is configured to be removed from the surface portion leaving no more than 5% of the second adhesive layer on the surface portion.

Embodiment 38. The method of any of embodiments 21-37, wherein the decorative patch is configured to be removed from the surface portion leaving no more than 2% of the second adhesive layer on the surface portion.

Embodiment 39. The method of any of embodiments 21-39, wherein the second adhesive layer of the decorative patch comprises a zinc-oxide and a rubber.

Embodiment 40. Any of the methods or decorative patches of any of embodiments 1-39, wherein the decorative patches is capable of being removed from a surface portion of the cast or other device after being adhered to a surface portion for at least 24 hours, at least 48 hours, at least one week, or even two weeks or longer while leaving no more than 10%, no more than 5%, or no more than 2% of the second adhesive layer on the surface portion.

Embodiment 41. Any of the methods or decorative patches of any of embodiments 1-40, wherein the decorative patches are capable of being removed after being adhered to a surface portion for at least 24 hours, at least 48 hours, at least one week, or even two weeks or longer, with at least 90%, at least 95%, or at least 98% of the second adhesive layer being removed with the patch, leaving little to no residue on the surface portion.

Embodiment 42. Any of the methods or decorative patches of any of embodiments 1-41, wherein at least 98% of the entire outer perimeter portion of the second adhesive layer of the decorative patch is capable of remaining adhered to the surface portion of the cast or other object for at least one week.

Embodiment 43. Any of the methods or decorative patches of any of embodiments 1-42, wherein the first material layer and the second adhesive layer compose a moleskin adhesive.

Embodiment 44. Any of the methods or decorative patches of any of embodiments 1-43, wherein the surface portion of the cast comprises an exterior surface portion of the cast.

Embodiment 45. Any of the methods of embodiments 21-44, wherein the decorative patches are not applied to skin.

Embodiment 46. Any of the methods or decorative patches of embodiments 1-45, wherein the decorative patch is capable of remaining self-adhered to the surface portion of the cast without peeling for at least 24 hours.

Embodiment 47. A kit, comprising: a set of decorative patches for removably adhering to a cast or other device, wherein each decorative patch of the set of decorative patches comprises: (a) a first material layer having a first side and a second side; and (b) a second adhesive layer applied to the second side of the first material layer.

Embodiment 48. The kit of embodiment 47, wherein at least one patch of the set of decorative patches comprises one or more designs drawn or printed on the first side.

Embodiment 49. The kit of any of embodiments 47-48, wherein at least one patch of the set of decorative patches comprises one or more designs drawn on the first side.

Embodiment 50. The kit of any of embodiments 47-49, wherein at least one patch of the set of decorative patches comprises one or more designs printed on the first side.

Embodiment 51. The kit of any of embodiments 47-50, wherein at least one patch of the set of decorative patches comprises a blank or outlined surface portion on the first side configured to be drawn or printed on.

Embodiment 52. The kit of any of embodiments 47-51, wherein the first material layer comprises a cotton.

Embodiment 53. The kit of any of embodiments 47-52, wherein the first material layer comprises a cotton sateen cloth fabric.

Embodiment 54. The kit of any of embodiments 47-53, wherein the first material layer comprises a napped cotton.

Embodiment 55. The kit of any of embodiments 47-54, wherein the first material layer comprises at least one of a leather, a felt, a linen, a cotton, a nylon, a flannel, and a latex.

Embodiment 56. The kit of any of embodiments 47-55, wherein the decorative patch has a thickness of between 20-50 mils.

Embodiment 57. The kit of any of embodiments 47-56, wherein the decorative patch has a thickness of between 30-40 mils.

Embodiment 58. The kit of any of embodiments 47-57, wherein the second adhesive layer is applied to at least 98% of the second side of the first material layer.

Embodiment 59. The kit of any of embodiments 47-58, wherein the second adhesive layer is applied to an entire outer edge of the second side of the first material layer.

Embodiment 60. The kit of any of embodiments 47-59, wherein the second adhesive layer comprises a zinc-oxide.

Embodiment 61. Any of the kits of embodiments 47-61, wherein at least one patch of the set of decorative patches is capable of remaining self-adhered to the surface portion of the cast without peeling for at least 24 hours.

Embodiment 62. Any of the kits of embodiments 47-61, wherein each patch of the set of decorative patches is capable of remaining self-adhered to the surface portion of the cast without peeling for at least 24 hours.

Embodiment 63. Any of the kits of embodiments 47-61, wherein each patch of the set of decorative patches is capable of remaining self-adhered to the surface portion of the cast without peeling for at least 48 hours, Embodiment 64. Any of the methods of embodiments 14-44, further comprising, prior to removing the backing from the decorative patch, drawing one or more designs on the first material layer of the decorative patch.

Embodiment 65. Any of the methods of embodiments 14-44 or 64, further comprising, prior to removing the backing from the decorative patch, printing one or more designs on the first material layer of the decorative patch.

Embodiment 66. Any of the methods of embodiments 14-44 or 64-65, further comprising, prior to removing the backing from the decorative patch, stamping one or more designs on the first material layer of the decorative patch.

Embodiment 67. Any of the methods of embodiments 64-66, further comprising, prior to drawing, printing or stamping one or more designs on the first material layer of the decorative patch, determining a design preference of an individual wearing the cast.

Embodiment 68. Any of the methods of embodiments 14-44 or 64-67, further comprising removing the decorative patch from the surface portion of the cast, removing a backing from a second decorative patch comprising a material layer and an adhesive layer, and applying the adhesive layer to at least a portion of the surface portion of the cast, wherein the second decorative patch is capable of remaining adhered to the surface portion of the cast without peeling for at least 24 hours.

Embodiment 69. Any of the methods of embodiments 14-44 or 64-67, further comprising removing a backing from a second decorative patch comprising a material layer and an adhesive layer, and applying the adhesive layer to a second surface portion of the cast, wherein the second decorative patch is capable of remaining adhered to the second surface portion of the cast without peeling for at least 24 hours.

Embodiment 70. Any of the methods of embodiments 14-44 or 64-69, further comprising removing a backing from a third decorative patch comprising a material layer and an adhesive layer, and applying the adhesive layer to a third surface portion of the cast, wherein the second decorative patch is capable of remaining adhered to the third surface portion of the cast without peeling for at least 24 hours.

Embodiment 71. Any of the methods of embodiments 69-70, wherein the first and second portions are different portions of the cast.

Embodiment 72. Any of the kits of embodiments 47-63, further comprising a drawing device, Embodiment 73. A kit of embodiment 72, wherein the drawing device comprises a crayon, pencil, marker, glitter pen, paint, or paint pen.

Embodiment 74. A kit of any of embodiments 47-63 or 72-73, wherein the set of decorative patches comprises at least 5 decorative patches.

Embodiment 75. A kit of any of embodiments 47-63 or 72-74, wherein a single release liner or backing paper sheet carries each decorative patch of the set of decorative patches preventing the adhesive layer of the decorative patches from prematurely adhering to an object.

Embodiment 76. A kit of any of embodiments 47-63 or 72-75, wherein each decorative patch of the set of decorative patches has a unique shape that differs from the other patches of the set.

Embodiment 77. A method of providing non-pharmacological analgesia to a patient having a cast after a medical procedure by applying a decorative patch to a surface portion of the cast, wherein the decorative patch is capable of remaining adhered to the surface portion of the cast without peeling through a pain management period after the cast is put on the patient.

Embodiment 78. The method of embodiment 77, wherein the application of the decorative patch results in lower pain score during the pain management period.

Embodiment 79. The method of embodiment 78, wherein the pain score during the pain management period is a VAS score.

Embodiment 80. The method of embodiment 78, wherein the pain score during the pain management period is a FLACC score.

Embodiment 81. The method of any of embodiments 77-79, wherein the application of the decorative patch results in less need of pharmacological analgesia.

Embodiment 82. The method of any of embodiments 77-79, wherein the application of the decorative patch results in no need of pharmacological analgesia.

Embodiment 83. The method of any of embodiments 77-82, wherein the pain management period is up to 12 hours after the cast is put on the patient.

Embodiment 84. The method of any of embodiments 77-82, wherein the pain management period is up to 24 hours after the cast is put on the patient.

Embodiment 85. The method of any of embodiments 77-82, wherein the pain management period is up to 36 hours after the cast is put on the patient.

Embodiment 86. The method of any of embodiments 77-82, wherein the pain management period is up to 48 hours after the cast is put on the patient.

Embodiment 87. The method of any of embodiments 77-82, wherein the pain management period is up to 60 hours after the cast is put on the patient.

Embodiment 88. The method of any of embodiments 77-82, wherein the pain management period is up to 72 hours after the cast is put on the patient.

Embodiment 89. The method of any of embodiments 77-82, wherein the pain management period is up to 96 hours after the cast is put on the patient.

Embodiment 90. The method of any of embodiments 77-82, wherein the pain management period is up to 120 hours after the cast is put on the patient.

Embodiment 91. The method of any of embodiments 77-90, wherein the decorative patch is applied by: removing a backing from a decorative patch comprising a first material layer and a second adhesive layer; and applying the second adhesive layer to the surface portion of the cast.

Embodiment 92. The method of embodiment 91, wherein the decorative patch is configured to be removed from the surface portion without leaving a residue of the second adhesive layer on the surface portion.

Embodiment 93. The method of any of embodiments 91-92, further comprising removing the decorative patch from the surface portion of the cast; and applying a second adhesive layer of a second decorative patch to the surface portion of the cast.

Embodiment 94. The method of any of embodiments 91-93, wherein the second decorative patch comprises a second material layer, and wherein the first material layer and the second material layer have different designs drawn or printed thereon.

Embodiment 95. The method of any of embodiments 91-94, wherein the surface portion comprises at least one of a fiberglass, a plaster, and a self-adherent wrap material.

Embodiment 96. The method of any of embodiments 91-95, further comprising drawing or printing a design on a first side of the first material layer with an ink.

Embodiment 97. The method of any of embodiments 91-96, wherein the first material layer comprises a fabric material, wherein the fabric material comprises a napped cotton, and wherein the second adhesive layer comprises a zinc-oxide.

Embodiment 98. The method of any of embodiments 91-97, wherein the first material layer of the decorative patch has a first side and a second side, and wherein the first side comprises a design drawn or printed thereon, and wherein the second adhesive layer is applied to the second side of the first material layer, and wherein the second adhesive layer comprises a zinc-oxide.

Embodiment 99. The method of any of embodiments 91-98, wherein the first material layer of the decorative patch comprises a cotton.

Embodiment 100. The method of any of embodiments 91-99, wherein the first material layer of the decorative patch comprises a cotton.

Embodiment 101. The method of any of embodiments 91-100, wherein the first material layer of the decorative patch comprises a cotton sateen cloth fabric.

Embodiment 102. The method of any of embodiments 91-101, wherein the first material layer of the decorative patch comprises at least one of a leather, a felt, a linen, a cotton, a nylon, a flannel, and a latex.

Embodiment 103. The method of any of embodiments 91-102, wherein the decorative patch has a thickness of between 20-50 mils.

Embodiment 104. The method of any of embodiments 91-103, wherein the decorative patch has a thickness of between 30-40 mils.

Embodiment 105. The method of any of embodiments 91-104, wherein the first material layer of the decorative patch comprises a first side and a second side, and wherein the second adhesive layer of the decorative patch is applied to at least 98% of the second side of the first material layer.

Embodiment 106. The method of any of embodiments 91-105, wherein the first material layer of the decorative patch comprises a first side and a second side, and wherein the second adhesive layer of the decorative patch is applied to an entire outer edge of the second side of the first material layer.

Embodiment 107. The method of any of embodiments 91-106, wherein the decorative patch is configured to be removed from the surface portion leaving no more than 5% of the second adhesive layer on the surface portion.

Embodiment 108. The method of any of embodiments 91-107, wherein the decorative patch is configured to be removed from the surface portion leaving no more than 2% of the second adhesive layer on the surface portion.

Embodiment 109. The method of any of embodiments 91-109, wherein the second adhesive layer of the decorative patch comprises a zinc-oxide and a rubber.

Thus, specific examples of decorative patches, kits, and methods of using the decorative patches have been disclosed. It should be apparent, however, to those skilled in the art that many more modifications besides those already described are possible without departing from the inventive concepts herein. While examples and variations of the many aspects of the inventive subject matter have been disclosed and described herein, such disclosure is provided for purposes of explanation and illustration only. Thus, various changes and modifications may be made without departing from the scope of the claims. The examples herein are not meant to be limiting in any way in converting the principles discussed in this disclosure into physical form, and are not necessarily to scale as may be used in a physical system. Like reference numerals refer to like parts in different views or embodiments.

Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

The terminology used herein is for the purpose of describing particular cases only and is not intended to be limiting. The below terms are discussed to illustrate meanings of the terms as used in this specification, in addition to the understanding of these terms by those of skill in the art. As used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Reference throughout this specification to "an embodiment" or "an implementation" means that a particular feature, structure, or characteristic described in connection with the embodiment is included in at least one embodiment or implementation. Thus, appearances of the phrases "in an embodiment" in various places throughout this specification are not necessarily all referring to the same embodiment or a single exclusive embodiment. Furthermore, the particular features, structures, or characteristics described herein may be combined in any suitable manner in one or more embodiments or one or more implementations.

The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more.

As used herein, and unless the context dictates otherwise, the term "coupled to" is intended to include both direct coupling (in which two elements that are coupled to each other contact each other) and indirect coupling (in which at least one additional element is located between the two elements).

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the inventive subject matter and does not pose a limitation on the scope of the disclosure otherwise claimed. No language in the specification should be construed as indicating any non-claimed element essential to the practice of the inventive subject matter.

Certain numerical values and ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

All structural and functional equivalents to the elements of the various aspects described throughout this disclosure that are known or later come to be known to those of ordinary skill in the art are expressly incorporated herein by reference and are intended to be encompassed by the claims.

Moreover, nothing disclosed herein is intended to be dedicated to the public regardless of whether such disclosure is explicitly recited in the claims. The words "assembly," "mechanism," "element," "device," and the like may not be a substitute for the word "means." As such, no claim element is to be construed as a means plus function unless the element is expressly recited using the phrase "means for."

What is claimed is:

1. A method of providing non-pharmacological analgesia to a patient having a cast after a medical procedure requiring the cast, comprising:

applying a decorative patch to a surface portion of the cast, wherein the decorative patch is capable of remaining adhered to the surface portion of the cast without peeling through a pain management period of at least 12 hours after the cast is put on the patient;

assessing a pain score associated with the patient during the pain management period, and administering based on lowering of the pain score, a lower dose of an analgesic to the patient during the pain management period relative to an amount of the analgesic that would have been administered if the decorative patch is not applied.

2. The method of claim 1, wherein the pain score is at least one of a visual analog scale (VAS) score and a face, legs, activity, cry, consolability (FLACC) score.

3. The method of claim 1, wherein the pain management period is up to 24 hours after the cast is put on the patient.

4. The method of claim 1, wherein the pain management period is up to 36 hours after the cast is put on the patient.

5. The method of claim 1, wherein the pain management period is up to 48 hours after the cast is put on the patient.

6. The method of claim 1, wherein the decorative patch comprises a first material layer and a second adhesive layer, and wherein applying the decorative patch comprises:

removing a backing from the decorative patch; and applying the second adhesive layer to the surface portion of the cast.

7. The method of claim 6, wherein the decorative patch is configured to be removed from the surface portion after the pain management period without leaving a residue of the second adhesive layer on the surface portion.

8. The method of claim 6, further comprising drawing or printing a design on a first side of the first material layer with an ink.

9. The method of claim 6, wherein the first material layer comprises a fabric material, wherein the fabric material comprises a napped cotton, and wherein the second adhesive layer comprises a zinc-oxide.

10. The method of claim 6, wherein the first material layer of the decorative patch has a first side and a second side, and wherein the first side comprises a design drawn or printed thereon, and wherein the second adhesive layer is applied to the second side of the first material layer, and wherein the second adhesive layer comprises a zinc-oxide.

11. The method of claim 6, wherein the first material layer of the decorative patch comprises a first side and a second side, and wherein the second adhesive layer of the decorative patch is applied to at least 98% of the second side of the first material layer.

12. The method of claim 6, wherein the first material layer of the decorative patch comprises a first side and a second side, and wherein the second adhesive layer of the decorative patch is applied to only a portion of the second side of the first material layer.

13. The method of claim 6, wherein the first material layer of the decorative patch comprises a first side and a second side, and wherein the second adhesive layer of the decorative patch is applied to an entire outer edge of the second side of the first material layer.

14. The method of claim 6, wherein the decorative patch is configured to be removed from the surface portion leaving no more than 2% of the second adhesive layer on the surface portion.

15. The method of claim 6, wherein the second adhesive layer of the decorative patch comprises a zinc-oxide and a rubber.

16. The method of claim 1, further comprising:

removing the decorative patch from the surface portion of the cast; and applying an adhesive layer of a second decorative patch to the surface portion of the cast.

17. The method of claim 1, wherein the surface portion comprises at least one of a fiberglass, a plaster, and a self-adherent wrap material.

18. The method of claim 1, wherein the decorative patch has a thickness of between 20-50 mils.

* * * * *